United States Patent
Damadian (10) Patent No.: US 6,249,695 B1
(45) Date of Patent: Jun. 19, 2001

(54) PATIENT MOVEMENT DURING IMAGE GUIDED SURGERY

(75) Inventor: Raymond V. Damadian, Woodbury, NY (US)

(73) Assignee: Fonar Corporation, Melville, NY (US)

(*) Notice: Subject to any disclaimer, the term of this patent is extended or adjusted under 35 U.S.C. 154(b) by 0 days.

(21) Appl. No.: 09/196,814

(22) Filed: Nov. 20, 1998

Related U.S. Application Data

(63) Continuation-in-part of application No. 08/975,913, filed on Nov. 21, 1997.
(60) Provisional application No. 60/066,798, filed on Nov. 26, 1997.

(51) Int. Cl.[7] .................................................. A61B 5/00
(52) U.S. Cl. ........................... 600/427; 5/610; 5/607; 5/608
(58) Field of Search ................................. 600/427, 407, 600/410; 378/98.2, 62; 5/610, 611, 607, 608, 609

(56) References Cited

U.S. PATENT DOCUMENTS

| | | | | |
|---|---|---|---|---|
| 4,021,028 | * | 5/1977 | Weber et al. | 269/325 |
| 5,013,018 | * | 5/1991 | Sicek et al. | 269/323 |
| 5,386,450 | * | 1/1995 | Ozawa | 378/98.2 |
| 5,419,325 | * | 5/1995 | Dumoulin et al. | 128/653.2 |
| 5,794,286 | * | 8/1998 | Scott et al. | 5/611 |

* cited by examiner

Primary Examiner—Marvin M. Lateef
Assistant Examiner—Eleni Mantis Mercader
(74) Attorney, Agent, or Firm—Lerner, David, Littenberg, Krumholtz & Mentlik, LLP (57) ABSTRACT

A interventional procedure is performed by advancing a probe into a patient and periodically acquiring magnetic resonance images depicting the probe and adjacent portions of the patient's body. The patient, or a part of the patient, is reoriented during the procedure to facilitate advancement of the probe as, for example, by changing the position or orientation of internal organs.

11 Claims, 5 Drawing Sheets

PATIENT MOVEMENT DURING IMAGE GUIDED SURGERY

The present application is a continuation-in-part of the aforementioned U.S. patent application Ser. No. 08/975,913 filed Nov. 21, 1997. The present application claims benefit of U.S. Provisional Patent Application 60/066,798, filed Nov. 26, 1997, the disclosure of which is also incorporated by reference herein. The present application incorporates by reference the entire disclosure of co-pending, commonly assigned U.S. patent application Ser. No. 07/993,072 filed Dec. 18, 1992 and incorporates by reference the entire disclosure of co-pending, commonly assigned U.S. patent application Ser. No. 08/975,913 filed Nov. 21, 1997.

BACKGROUND OF THE INVENTION

Traditional surgical procedures are conducted by making an incision in the patient's body to expose those organs which are to be treated. The physician can observe the treatment directly and can guide tools such as surgical instruments to the site requiring treatment by direct visual observation. In typical endoscopic procedures, an elongated probe having a visual observation device such as a lens and fiber optic system or a small television camera is inserted into the patient's body and guided to the desired treatment location using observation of the visual image acquired by the visual observation device. The observation device can also be used to monitor additional probes such as tools inserted through the bore of a hollow endoscope or separate surgical instruments advanced through the same or other orifices to the treatment location. Endoscopic procedures suffer from various limitations. They require relatively bulky optical elements at the distal end of the endoscope. Moreover, the physician must conduct the procedure based on a limited picture delivered by the optical system.

Image-guided interventional procedures have been developed. In image-guided procedures, an imaging device such as an x-ray device is employed to monitor the position of a probe within the body. In the simplest image-guided procedures, a fluoroscope can be used to observe the position of a radioopaque probe while the probe is inserted into the body. Fluoroscopic and other x-ray imaging modalities have serious drawbacks, including exposure of the patient and physician to ionizing radiation and inability or limited ability to image soft tissues. Accordingly, treatment methods relying on x-ray based imaging for guidance of an intrabody probe have been applied only in limited circumstances.

Magnetic resonance imaging offers the unique ability to obtain excellent images of all tissues in a patient's body without the use of ionizing radiation. MRI typically requires the use of a large magnet to apply a strong magnetic field in a patient receiving space, large enough to accommodate that region of the patient's body which is to be imaged. Some early types of MRI imaging apparatus using superconducting magnets had a patient-receiving space essentially surrounded by components of the apparatus, making it impractical to perform interventional procedures while the patient is being imaged. However, some current MRI apparatus provides an "open" environment so that a patient disposed in the imaging space of the apparatus is accessible to physicians and other medical personnel. For example, magnetic resonance imaging apparatus of the type illustrated in U.S. Pat. No. 5,754,085 provides open access to the patient so that a patient positioned within the magnet is readily accessible to a physician standing outside of the magnet, making it practical to perform MRI-guided interventional procedures. In such procedures, MRI images may be continually acquired while a probe such as a catheter, endoscopic instrument, or other device is advanced into the patient. The MRI images desirably show internal structures of the patient's body and also depict the probe.

The MRI images allow the physician to visualize the disposition of the probe relative to the organs and tissues of the body and allow the physician to maneuver the probe along a desired trajectory within the body. For example, the physician can use MRI images to guide a probe within a tubular or cavernous organ such as within the circulatory tract, digestive tract, respiratory tract or urinary tract. Also, the physician can guide a probe within soft tissue as the probe is advanced through the soft tissue as, for example, through muscle, lung tissue or the like. The MRI images can also be used to monitor the progress of the treatment being performed. For example, if particular tissues such as tumors are being removed, the MRI images can show the tumor in contrast to the surrounding tissue and can show the physician where additional tissue must be removed.

Despite all this progress in the art, still further improvements in image-guided interventional procedures would be desirable.

SUMMARY OF THE INVENTION

One aspect of the present invention provides methods of conducting image-guided medical procedures. A method according to this aspect of the invention includes the steps of advancing a probe within a patient and, during the probe-advancing step, periodically acquiring information defining an image of the probe and adjacent internal structures of the patient's body. Most preferably, the step of acquiring the image information is performed by magnetic resonance imaging. A method according to this aspect of the invention further includes the step of changing the orientation of the patient in response to the image information so as to facilitate the probe-advancing step. For example, the step of changing the orientation of the patient may include the step of changing the orientation of the patient so that tissue disposed in front of the probe along a desired probe path is displaced away from the probe path. For example, if an internal organ of the patient is disposed in front of the desired path of advancement of the probe, turning the patient to a new orientation may cause gravity to displace that organ to the surrounding portions of the patient's body and relative to the probe. Also, where a tubular organ such as a blood vessel is kinked or folded so that a straight or gently curving path along the tubular organ is blocked by the tissue at the kink or fold, the change in patient orientation can remove the kink or fold and thus take the blocking tissue away from the desired path of the probe. Alternatively or additionally, the step of changing the orientation of the patient may include the step of changing the orientation of the patient while the probe is disposed in the patient so as to alter the disposition of the probe. For example, the probe may be flexible and the step of changing the orientation of the patient is performed so that gravitational forces applied to the probe, to the surrounding tissues or both bend the probe to a more favorable configuration.

In particularly preferred methods according to this aspect of the invention, the patient's body is positioned on a support, and the step of changing the orientation of the patient includes the step of tilting the support. For example, the support may be tilted about a tilt axis substantially parallel with the long axis of the patient; around an inclination axis transverse to the long axis of the patient or both. In still further embodiments of the invention, the step of changing the orientation of the patient may include the step of moving one part of the patient's body relative to another part. For example, where a probe is advanced within the vasculature of a limb, a part of the limb may be moved relative to the torso or relative to another part of the limb so as to reconfigure the vascular system.

In the preferred methods according to this aspect of the invention, the orientation of the patient facilitates movement of the probe through the patient's body to the desired treatment location, with a minimum of damage to surrounding tissues. This benefit is particularly pronounced when the MRI is the imaging modality. The unique ability of MRI to provide details of soft tissue images, coupled with the ability to reposition soft tissues by reorienting the patient provides a particularly valuable combination.

These and other objects, features and advantages of the present invention will be more readily apparent from the detailed descriptions set forth below, taken in conjunction with the accompanying drawings.

DETAILED DESCRIPTION OF THE DRAWINGS

DETAILED DESCRIPTION OF THE PREFERRED EMBODIMENTS

Apparatus utilized in a method according to one embodiment of the invention includes a magnetic resonance imaging instrument incorporating a static field magnet 10. The particular static field magnet depicted in FIGS. 1 and 2 includes a ferromagnetic frame 12 incorporating top and bottom ferromagnetic pole supports 14 and 16; a pair a ferromagnetic poles 18 and 20 projecting downwardly and upwardly from pole supports 14 and 16 respectively and a pair of connecting elements 22 and 24 supporting the upper pole support above the lower pole support. The static field magnet further includes a source of magnetic flux such as a pair of coils 26 and 28 encircling the pole stems 18 and 20, respectively. The poles 18 and 20 define a patient receiving gap 30 between them. The components of the static field magnet are arranged so that they define a working space 32 extending at least partially around the poles within the magnet structure. Working space 32 is sufficient size to accommodate a physician or other attendant 34 of normal size so that the physician or attendant can be positioned immediately adjacent the patient receiving gap 30 and can attend to a patient 36 disposed within a gap 30.

The magnetic resonance imaging instrument further includes gradient coils 38 and radio frequency antennas 40, schematically indicated in the drawings, as well as a conventional imaging electronic system 42. System 42 includes conventional components for driving gradient coils 38 so as to superimpose gradient fields varying in space within gap 30 on the static, substantially constant fields provided by the static field magnet 10. The imaging electronics system 42 also includes conventional devices for actuating the RF antenna 40 to transmit radio frequency excitation signals in the gap and to receive weak radio frequency signals, commonly referred to as magnetic resonance signals, emitted from materials within the gap. The imaging electronics system 42 further includes a computer for coordinating the operation of these components and reconstructing an image of a patient disposed within the gap from the magnetic resonance signals. These components of the apparatus are well-known in the magnetic resonance art and accordingly are not discussed in detail herein. The imaging electronics system is linked to displays 44 such as cathode ray tubes or other conventional display device. Displays 44 are mounted at locations where they are visible to physicians 34 disposed within the working space 32. Of course, one display device, or more than one display may be provided.

As further described in the aforementioned co-pending, commonly assigned applications, the magnet structure defines portions of a room, with a floor 60 and ceiling 62. The lower pole 20 projects upwardly from the floor, whereas the upper pole 18 projects downwardly from the ceiling of the room. The working space 32 and patient-receiving gap 30 is disposed within the room.

Figure 2:
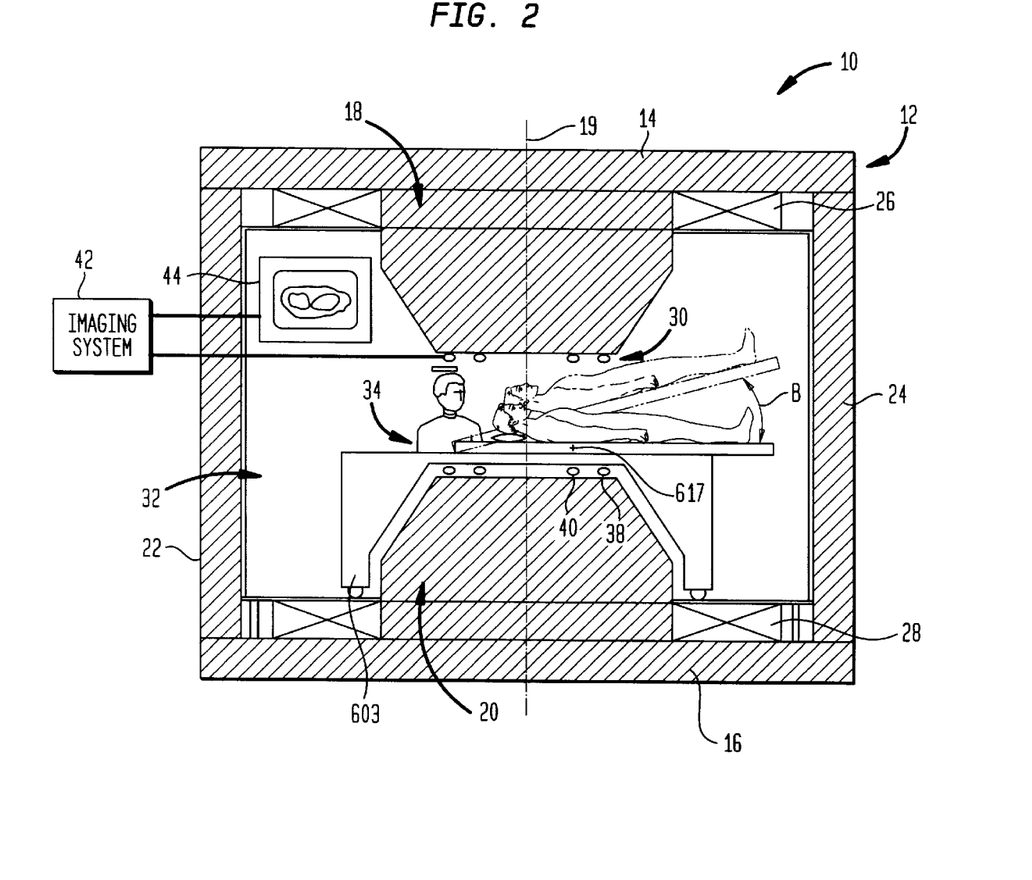
FIG. 2 is a diagrammatic, sectional view taken along line 2—2 in FIG. 1.
Figure 3A:
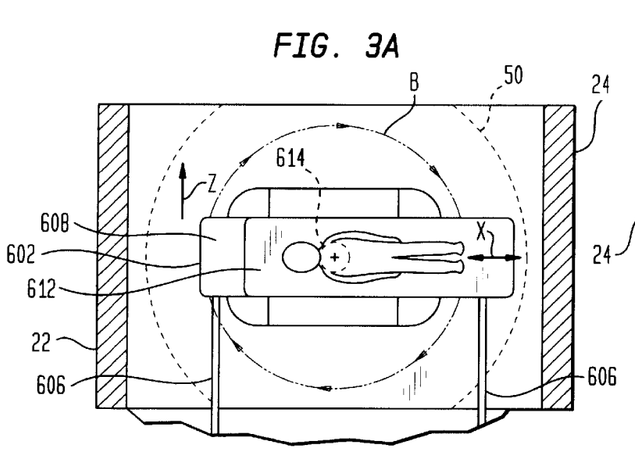
FIGS. 3A–3D are diagrammatic sectional views taken along line 3—3 in FIG. 1, depicting elements of the apparatus in moved positions.
Figure 3B:
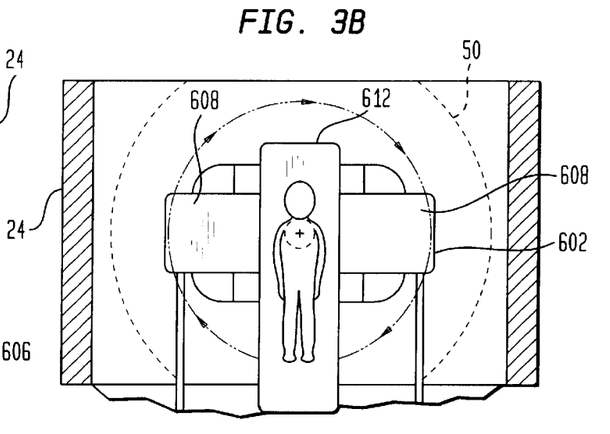
Figure 3C:
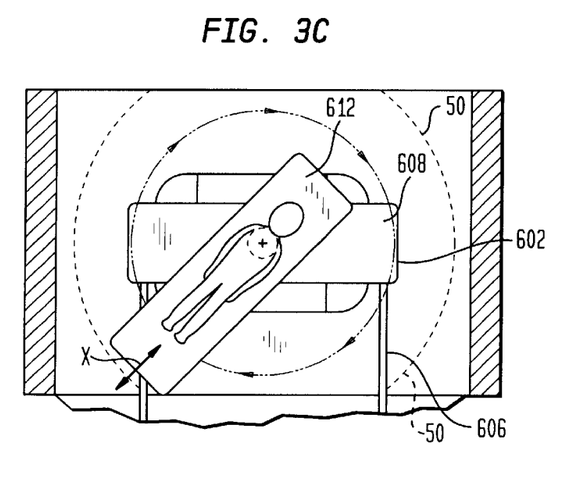
Figure 3D:
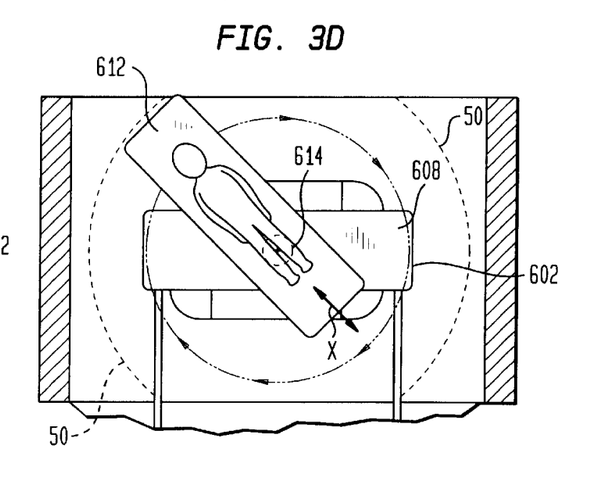

A patient positioning device 600 is used with the magnetic resonance imaging system and magnet to position the patient relative to the poles and magnet gap. Device 600 desirably is formed from non-magnetic materials such as polymers. The positioning device includes a chassis 602 mounted on wheels 604. A pair of rails 606 extend along the floor 60 of the room and also extend outwardly from the room onto the adjacent floor of the building. Wheels 604 run along these rails so that chassis 602 can be moved along a first horizontal axis, denoted by arrow Z, transverse to the polar axis 19 [mention earlier] of the magnet. As best seen in FIG. 2, chassis 602 includes a pair of vertically-extensive end portions 603 which lie on opposite sides of the lower pole 20 when the chassis is aligned with the polar axis 19 of the magnet. A bridge portion 605 of the chassis extends between the end portions, and overlies pole 20 when the chassis is aligned with the polar axis. Brakes (not shown) on wheels 604, or other devices for holding chassis 602 in position on the rails may be provided. In addition, the rails or the adjacent portions of the floor may be provided with graduations, and chassis 602 may be provided with a point or other index mark so that the chassis can be brought to a preselected disposition in the first movement or Z direction. Other positioning devices, such as a screw jack, fixed or adjustable stop or optical positioning system may be employed to locate and index the position of the chassis relative to the floor and the magnet frame.

An upper member 608 is mounted on chassis 602. A screw jack 610 (FIG. 1) or other mechanical positioning system such as a hydraulic or pneumatic cylinder, lever system or the like is also provided for moving upper member 608 vertically, in the axial or Y direction, parallel to the polar axis 19 of the magnet. Positioning device 610 may be arranged to displace upper member 608 relative to the remainder of the chassis. Alternatively, upper member 608 may be fixed to the remainder of the chassis and positioning device 610 may be adapted to move the chassis 602 relative to wheels 604. An elongated, movable support 612 is mounted for pivoting movement relative to the chassis and upper member 608 around a pivot 614 (FIG. 5A). Pivot 614 is close to the center of the chassis. Thus, when the chassis is positioned in the Z direction so that the center of the chassis is coincident with the polar axis 19, the pivot 614 is also close to the polar axis. Movable support 612 is also mounted for sliding motion relative to upper member 608 and chassis 602 in a longitudinal direction X, parallel to the long direction of the support itself. Thus, as seen in FIGS. 3A through 3D, the movable support 612 can swing in pivoting motion around pivot 614 so as to orient the longitudinal direction X at any desired angle to the first movement direction Z. Thus, the longitudinal direction X of the movable support can be oriented in any direction relative to the long axis of the rectangular poles 30 and 20. By moving the movable support relative to the chassis 602 in its longitudinal direction, various locations along the length of the movable support 612 can be aligned with the polar axis 19 of the magnet.

Figure 1:
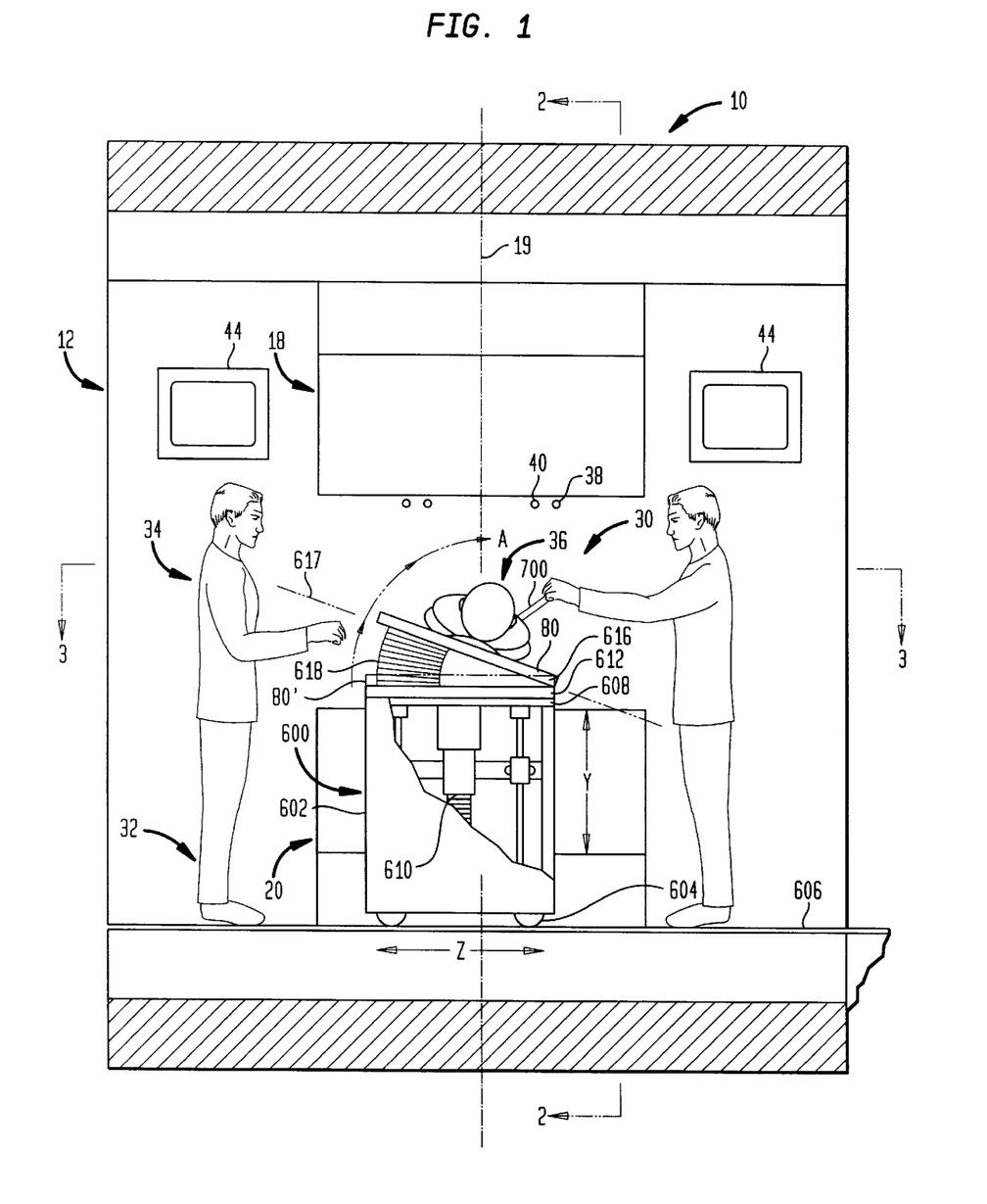
FIG. 1 is a diagrammatic, sectional elevational view of apparatus utilized in a method according to one embodiment of the invention.
Figure 4:
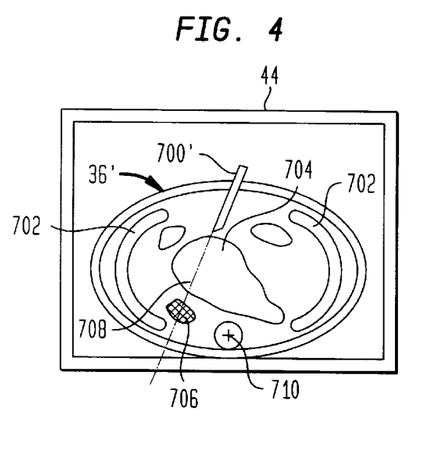
FIGS. 4 and 5 are diagrammatic depictions of images acquired in the methods of FIGS. 1–2.

Additionally, the litter or actual patient-carrying device 80 is mounted to the movable support 612 for pivoting movement around a tilt axis 616 parallel to the longitudinal or X direction of the movable support. Thus, as seen in FIG. 4, the tilt axis 616 extends into and out of the plane of the drawing. A tilt actuation device 618, such as a pneumatic bladder or pneumatic cylinder, screw jack, or wedge jack, is provided for tilting the litter through a range of tilt angles A (FIG. 1). The patient support is also pivotable relative to the movable support about an inclination axis 617 transverse to the lengthwise direction of the support and transverse to the tilt axis. An inclination actuator (not shown) similar to the tilt actuator is provided for pivoting the support about the inclination axis through a range of inclination angles B (FIG. 2). This allows positioning of the patient in a Trendlenbug position as indicated in broken lines in FIG. 2, wherein the patient's thorax is lowered relative to the abdomen or in a counter-Trendlenburg position, wherein the thorax is elevated relative to the abdomen. Thus, the patient positioner 600 provides litter or support 80 with movement in six degrees of freedom: translation in a first lateral direction Z transverse to the polar axis; translation in the X or longitudinal direction of the movable support 612, also transverse to polar axis 19 and at an arbitrary angle to the first or Z direction; rotation in a horizontal plane transverse to the polar axis so as to orient the longitudinal direction X at any angle B relative to the long axes of the poles; elevation or axial movement Y (FIG. 4) parallel to the polar axis; tilt to any desired angle A to the horizontal plane; and inclination B so as to raise either end of the support. This provides extraordinary versatility in positioning of the patient relative to the magnet. For example, as seen in solid lines in FIG. 2, the head and neck of the patient is substantially aligned with the polar axis. Translation in the longitudinal direction allows positioning of the feet adjacent the polar axis, as seen in broken lines in FIG. 2. Other arbitrary positions of the patient relative to the polar axis and relative to the remainder of the magnet are also shown in FIGS. 3A through 3D. As described in greater detail in the copending, commonly assigned applications, the magnet of the MRI apparatus provides a large clearance between the poles. Desirably, the vertical dimension of the gap, measured between the poles, at least about 17.5 inches and more desirably about 36 inches. The large clearance within the magnet provided by the ferromagnetic frame contributes to the positioning versatility and facilitates the methods discussed below. Thus, the large vertical dimension of the gap provides enough room to tilt the patient/s body through substantial angles A and B. Because the connecting elements are spaced at a radial distance R from the polar axis of about seven feet or more, longitudinal movement of the patient relative to the frame can be accommodated over a range sufficient to position essentially any part of the patient's body at the polar axis.

In a method according to one embodiment of the invention, a patient 36 is disposed by the patient support 80 and maintained within the gap 30 of the magnetic resonance imaging apparatus. A physician 34 standing adjacent to patient and adjacent gap 30 inserts a probe 700 into the patient's body. Patient support 80 is initially at a flat position indicated in broken lines at 80' in FIG. 1. As the physician inserts the probe, the magnetic resonance imaging apparatus operates to acquire an image of the patient and the probe. Probe 700 is desirably formed from a non-ferromagnetic material having MRI response different from the MRI response of the body tissues in the region to be imaged. Many MRI images are based on the response of hydrogen nuclei (protons). If probe 700 is formed in whole or in part from a hydrogen-free material such as a non-ferromagnetic metal, the probe will show zero response, where the surrounding tissues will show some response. The image depicted on screen 44 is a map of MRI response versus location, with response shown as color and/or brightness at each location on the screen, the probe will appear as a contrasting object superposed on the patient's tissues. For example, one form of MRI image is the so-called "proton density" image, in which the brightness or color of each spot on the image represents the amount of hydrogen present at the corresponding location in the patient's body. A probe formed from a hydrogen-free material such as a metal will show as a region of zero proton density, whereas the surrounding tissues typically have substantial hydrogen content. Other forms of MRI images include so-called T1 and T2 relaxation time images. In these images, the brightness or color of each spot on the displayed image represents a property of hydrogen nucleii at the corresponding location in the body referred to as T1 relaxation time or T2 relaxation time. These properties, in turn, vary with the nature of the chemical compounds containing the hydrogen nucleii. If probe 700 is formed from synthetic polymers, the relaxation times of the hydrogen nucleii constituting the probe will be markedly different from the relaxation times of the hydrogen nucleii in compounds such as water constituting the bodily tissues. Here again, the depiction 700' of probe 700 can be readily differentiated from the depictions of bodily tissues. The image of the patient also shows internal organs such as bony structures 702 and soft tissues 704.

Figure 5:
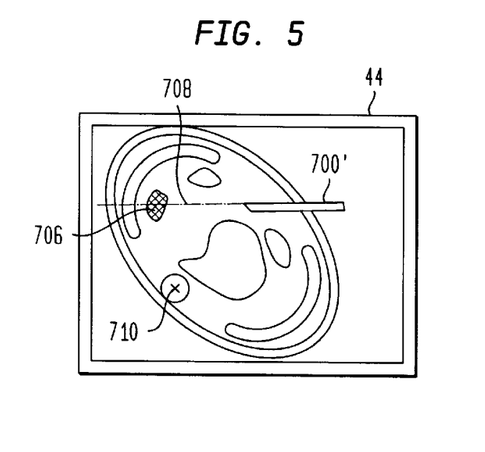

In the particular procedure illustrated, the physician is seeking to advance the probe to a lesion 706 along a trajectory 708. Organ 704 extends across the trajectory. As the physician is advancing the probe, he or she can see that organ 704 is blocking the desired path or trajectory 708 of the probe. While the system continues to acquire images of the patient, the physician actuates the patient positioning system 600 to tilt the patient support 80 about the tilt axis 616, thereby tilting the entire body of the patient about the patient's longitudinal axis 710. The image acquired when the patient is in this moved position is depicted schematically in FIG. 5. In this moved position, organ 704 has moved, under the influence of gravity, out of path 708, so that the position can advance the probe along path 708 to lesion 706. Because the physician can continually observe the internal structures of the patient, including the soft tissues, using the MRI apparatus and can continually readjust the position of the patient to move internal structures, the physician can advance probe 700 to the desired location with a minimum of tissue damage.

Figure 6:
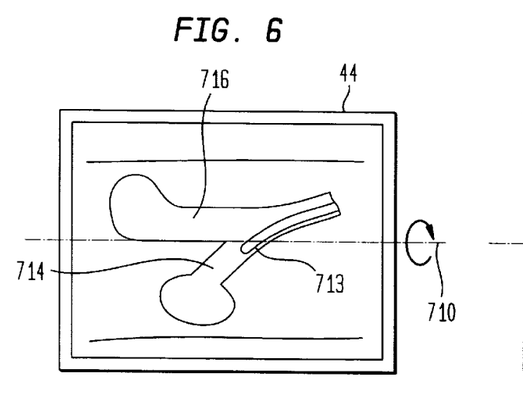
FIGS. 6 and 7 are diagrammatic depictions of images acquired in a method according to a further embodiment of the invention.
Figure 7:
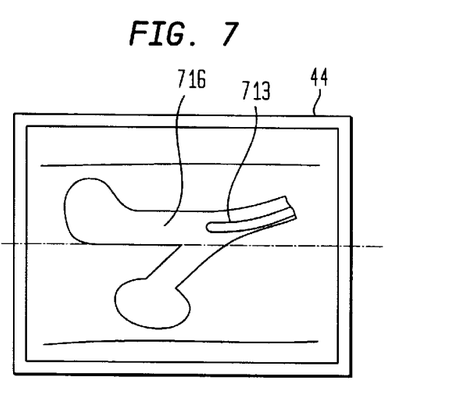

The method may include numerous repositionings of the patient so as to place the organs in the desired position at each stage of the treatment. For example, the tip of a probe may be threaded past an organ and the patient may then be turned once again so as to move another organ out of the way of the probe tip. As shown schematically in FIGS. 6 and 7, movement of the patient may also be used to deform the probe. Thus, in FIG. 6 the flexible probe 713 such as a flexible catheter or endoscope is being threaded within a cavernous organ such as the bronchial tract. The physician notes that the probe is bent toward an undesired branch 714 of the bronchial tract rather than into the desired branch 716. By tilting the patient about longitudinal axis 710, the patient tilts the desired branch 716 downwardly. The tilting motion is also applied to the flexible probe 713. Thus, the tip of probe 713 bends toward the downwardly tilted side and thus aligns itself with the desired passage 716. The same principles can be applied using tilting movements about other axes as, for example, about the inclination axis 617.

Figure 8:
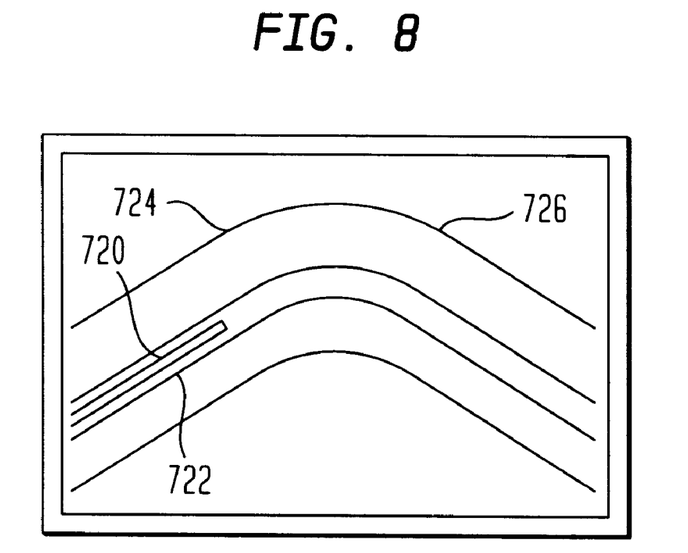
FIGS. 8 and 9 are diagrammatic depictions of images acquired in a method according to yet another embodiment of the invention.
Figure 9:
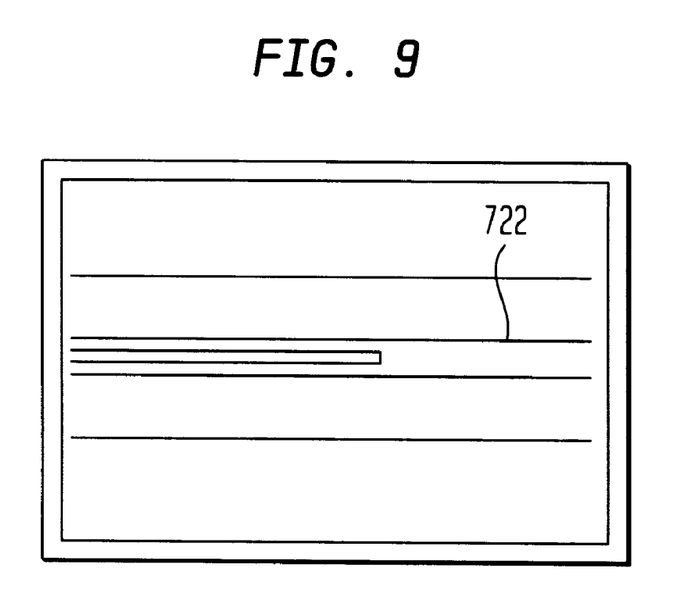

It is not necessary to tilt the entirety of the patient's body. For example, where a limb or other portion of the patient's body is being treated, that portion alone may be tilted. As depicted in FIGS. 8 and 9, a probe 720 is being advanced through a tubular organ such as a blood vessel 722 extending through a first portion 724 and a second portion 726 of a limb such as an arm or leg. In the position indicated in FIG. 8, the joint of the limb is bent so that the tubular blood vessel 722 is also bent. Thus, tissues such as the blood vessel wall lie in the path of advancement of probe 720. Using the guidance provided by MRI imaging, the physician can manipulate the limb to the position indicated in FIG. 9, in which the tubular blood vessel is aligned with the path of the probe 720. The simplified, schematic views shown in the drawings do not fully show all of the complexities encountered in anatomical structures. However, the ability of MRI imaging to provide full depictions of soft tissues and other tissues within the body are coupled with the ability to reorient body structures during the procedure, allows the physician to accommodate the wide range of anatomical complexities.

Methods according to this aspect of the present invention can be practiced utilizing other magnetic resonance imaging instruments. Desirably, the magnetic resonance imaging instrument provides a large patient-receiving gap and good access to the patient while the patient is exposed in the gap. For example, as described in the preferred embodiments of the aforementioned U.S. Pat. No. 5,754,085, may be employed. Also, the invention can be practiced using more than one probe simultaneously. The probe may be essentially any instrument to be inserted into the patient's body as, for example, catheters, endoscopic instruments, trocars, needles and conventional surgical instruments.

In the embodiments discussed above, the image of the probe is acquired by the MRI system itself during the same imaging sequences used to create the images of the patient. However, this is not essential. A wide variety of systems are known for tracking the locations of instruments in a known frame of reference as, for example, in the frame of reference of the magnetic resonance imaging instrument. Systems of this nature can use magnetic, radiofrequency, ultrasonic or other signals transmitted to or from a device mounted on the probe to determine the location and/or orientation of the probe in the fixed frame of reference. The position and orientation of the probe can be determined using these systems, and a representation of the probe can be superposed on an MRI image of the patient based upon the position and/or orientation acquired in this fashion and data defining the configuration of the probe.

According to the broadest compass of the invention, imaging other than magnetic resonance imaging, such as X-ray, CAT, ultrasound or other imaging modalities may be employed, however, such other imaging modalities are distinctly less preferred, as they lack the capabilities of MRI imaging discussed above.

As these and other variations and combinations of the features discussed above can be utilized without departing from the present invention as defined by the claims, the foregoing description of the preferred embodiment should be taken by way of illustration rather than by way of limitation of the invention as defined in the claims.

What is claimed is:

1. A method of conducting an image-guided medical procedure comprising the steps of:
   (a) advancing a probe within a patient along a desired path;
   (b) during said probe advancing step, periodically acquiring image information, said image information including an image of the probe and adjacent internal structures of the patient's body; and
   (c) changing the orientation of at least a part of the patient in response to said image information so that tissue is displaced away from the path so as to facilitate said probe-advancing step.

2. A method as claimed in claim 1 wherein said step of periodically acquiring image information is performed at least in part by periodically acquiring magnetic resonance images.

3. A method as claimed in claim 2 wherein said step of periodically acquiring magnetic resonance images is performed so that magnetic resonance information acquired in each such image includes information depicting at least a portion of the probe together with information depicting internal structures of the patient's body.

4. A method as claimed in claim 3 wherein said magnetic resonance information depicts soft tissues within the patient's body.

5. A method as claimed in claim 1 wherein said step of acquiring image information includes the step of periodically acquiring information about the disposition of one or more points on the probe and constructing a representation of the probe based on the disposition of said one or more points and information about the configuration of the probe.

6. A method as claimed in claim 1 wherein said step of changing the orientation of the patient includes the step of changing the orientation of the patient so that tissue disposed in front of the probe along the desired path is displaced away from the desired path.

7. A method as claimed in claim 1 wherein said step of changing the orientation of the patient includes the step of changing the orientation of the patient while the probe is embedded in the patient so as to alter the disposition of the probe within the patient.

8. A method as claimed in claim 1 further comprising the step of disposing a patient on a support, said step of changing the orientation of the patient including the step of tilting the support.

9. A method as claimed in claim 8 wherein said step of tilting the support includes the step of tilting the support about a tilt axis substantially parallel with the long axis of the patient.

10. A method as claimed in claim 8 wherein said step of tilting the support includes the step of tilting the support about an inclination axis transverse to the long axis of the patient.

11. A method as claimed in claim 1 wherein said step of changing the orientation of at least a part of the patient includes the step of moving one part of the patient relative to another part of the patient.

* * * * *

UNITED STATES PATENT AND TRADEMARK OFFICE
CERTIFICATE OF CORRECTION

PATENT NO. : 6,249,695 B1  
DATED : June 19, 2001  
INVENTOR(S) : Raymond V. Damadian It is certified that error appears in the above-identified patent and that said Letters Patent is hereby corrected as shown below:

<u>Title page,</u>  
Item [74], delete "Krumholtz" and insert -- Krumholz --.  
Item [57], ABSTRACT,  
Line 1, delete "A" and insert -- An --.

<u>Column 2,</u>  
Line 57, after "both" insert -- , --.

<u>Column 3,</u>  
Line 46, delete "a" and insert -- of --.

<u>Column 4,</u>  
Line 15, delete "device" and insert -- devices --.  
Line 18, after "display" insert -- , --.  
Line 36, delete "mention" and insert -- mentioned --.  
Line 50, after "system" insert -- , --.

<u>Column 5,</u>  
Line 56, before "at" insert -- is --.  
Line 61, delete "patient/s" and insert -- patients --.

<u>Column 7,</u>  
Line 44, before "may" insert -- "ferromagnetic yoke magnets having large patient-receiving gaps to provide open access to the patient --.

Signed and Sealed this

Second Day of September, 2003

JAMES E. ROGAN  
*Director of the United States Patent and Trademark Office*